United States Patent [19]

Marshall et al.

[11] Patent Number: 5,686,272
[45] Date of Patent: Nov. 11, 1997

[54] AMPLIFICATION OF RNA SEQUENCES USING THE LIGASE CHAIN REACTION

[75] Inventors: Ronald L. Marshall, Zion; John J. Carrino, Gurnee, both of Ill.; Joann C. Sustachek, Racine, Wis.

[73] Assignee: Abbott Laboratories, Abbott Park, Ill.

[21] Appl. No.: 356,287

[22] PCT Filed: May 24, 1993

[86] PCT No.: PCT/US93/04863

§ 371 Date: Feb. 22, 1995

§ 102(e) Date: Feb. 22, 1995

[87] PCT Pub. No.: WO93/24656

PCT Pub. Date: Dec. 9, 1993

Related U.S. Application Data

[63] Continuation-in-part of Ser. No. 891,543, May 29, 1992, abandoned.

[51] Int. Cl.[6] .............................. C12P 19/34; C12Q 1/68; C07H 21/04
[52] U.S. Cl. .......................... 435/91.2; 435/6; 435/91.1; 435/91.52; 435/810; 536/24.3; 935/77; 935/78
[58] Field of Search .................... 435/6, 91.1, 91.2, 435/91.52, 810; 536/24.3; 935/77, 78

[56] References Cited

U.S. PATENT DOCUMENTS

| | | | |
|---|---|---|---|
| 4,988,617 | 1/1991 | Landegren et al. | 435/6 |
| 5,185,243 | 2/1993 | Ullman et al. | 435/6 |
| 5,427,930 | 6/1995 | Birkenmeyer et al. | 435/91.52 |

FOREIGN PATENT DOCUMENTS

| | | | |
|---|---|---|---|
| 0473155 | 3/1992 | European Pat. Off. | 435/6 |
| 8606414 | 11/1986 | WIPO | 435/5 |
| 9001069 | 2/1990 | WIPO | 435/6 |
| 9110746 | 7/1991 | WIPO | 435/6 |
| 9202642 | 2/1992 | WIPO | 435/5 |
| 9219743 | 11/1992 | WIPO | |

OTHER PUBLICATIONS

Blumberg, B. M., et al., "Human Immunodeficiency Virus Type 1 nef Quasispecies in Pathological Tissue", *Journal of Virology*, 66(9):5256–5264 (1992).

Marshall, R. L., et al., "Detection of HCV RNA by the Asymmetric Gap Ligase Chain Reaction", 6189 *PCR Methods and Applications*, 2:80–84 (1994).

Innis et al., eds. "PCR Protocols: A Guide to Methods and Applications," (1990) Academic Press, Inc. pp. 21–27.

Sokolov Nuc. Acids Res. 18(12):3671, 1990.

*Primary Examiner*—W. Gary Jones
*Assistant Examiner*—Paul B. Tran
*Attorney, Agent, or Firm*—Thomas D. Brainard; Paul D. Yasger

[57] ABSTRACT

The present invention involves a method of amplifying RNA by producing complementary DNA (cDNA) by reverse transcription of RNA, and amplification of the cDNA sequences. The analysis of the amplified material facilitates the detection of pathogens and disease states associated with the presence of particular nucleic acid sequences, so the present invention is important in medical diagnostic procedures. A method of producing cDNA of predetermined length is also disclosed.

28 Claims, 2 Drawing Sheets

RNA Target sequence:
    ----CACCAUAGAUCACUCCCCUGUGAGGAACUACUGUCUUCACGCAGAAACGGU- Four Gap LCR Probes:
```
                       2                                3
5' fluor- CACCATAGATCACTCCCCTGTGAGGAA    ACTGTCTTCACGCAGAAACGGT-biotin 3'
3' fluor- GTGGTATCTAGTGAGGGGACA          GATGACAGAAGTGCGTCTTTGCCA-biotin 5'
                       4                                1
```

Amplification:

```
RNA ----CACCAUAGAUCACUCCCCUGUGAGGAACUACUGUCUUCACGCAGAAACGGU-- RNA
                                    GATGACAGAAGTGCGTCTTTGCCA
                                            probe 1
```

Reverse Transcriptase    ↓
    dCTP,dTTP

```
RNA--- CACCAUAGAUCACUCCCCUGUGAGGAACUACUGUCUUCACGCAGAAACGGU-- RNA
                                ctccttGATGACAGAAGTGCGTCTTTGCCA
                                        probe 1
```

DNA Polymerase    ↓    Denaturation and reannealing to

DNA Ligase               other 3 DNA probes extension by polymersase and
                                 ligation

```
CACCATAGATCACTCCCCTGTGAGGAActACTGTCTTCACGCAGAAACGGT
GTGGTATCTAGTGAGGGGACActccttGATGACAGAAGTGCGTCTTTGCCA
         ^ Ligation with DNA Ligase
```

↓

```
CACCATAGATCACTCCCCTGTGAGGAACTACTGTCTTCACGCAGAAACGGT
GTGGTATCTAGTGAGGGGACACTCCTTGATGACAGAAGTGCGTCTTTGCCA
```

↓

Cycles of denaturation and reannealing

DNA-DNA Amplification
FIG.2

SEQUENCE LISTING ( 1 ) GENERAL INFORMATION:

( i i i ) NUMBER OF SEQUENCES: 36

( 2 ) INFORMATION FOR SEQ ID NO: 1:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 1:

CCAGGCATTG AGCGGGTTGA TCC        23

( 2 ) INFORMATION FOR SEQ ID NO: 2:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear (i i) MOLECULE TYPE: Other nucleic acid (synthetic DNA)

(x i) SEQUENCE DESCRIPTION: SEQ ID NO: 2:

AATTGCCACG ACGACCGGGT CCTTTCTT                                                              28

(2) INFORMATION FOR SEQ ID NO: 3:

(i) SEQUENCE CHARACTERISTICS:
        (A) LENGTH: 20
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 3:

TCAACCCGCT CAATGCCTGG                                                                        20

(2) INFORMATION FOR SEQ ID NO: 4:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 4:

CCCGGTCGTC GTGGCAATT                                                                         19

(2) INFORMATION FOR SEQ ID NO: 5:

(i) SEQUENCE CHARACTERISTICS:
        (A) LENGTH: 24
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 5:

ACCGTTTCTG CGTGAAGACA GTAG                                                                   24

(2) INFORMATION FOR SEQ ID NO: 6:

(i) SEQUENCE CHARACTERISTICS:
        (A) LENGTH: 27
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 6:

CACCATAGAT CACTCCCCTG TGAGGAA                                                                27

(2) INFORMATION FOR SEQ ID NO: 7:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 7:

ACTGTCTTCA CGCAGAAACG GT 22

( 2 ) INFORMATION FOR SEQ ID NO: 8:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 8:

ACAGGGGAGT GATCTATGGT G 21

( 2 ) INFORMATION FOR SEQ ID NO: 9:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 9:

ACCAGCAGCC TGCCCAGGGC CT 22

( 2 ) INFORMATION FOR SEQ ID NO: 10:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 10:

GCAAGGTGAA TGTGGAAGAA GTTGGTGGTG 30

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 11:

GGCCCTGGGC AGGCTGCTGG 20

( 2 ) INFORMATION FOR SEQ ID NO: 12:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 12:

TTCTTCCACA TTCACCTTGC C 21

( 2 ) INFORMATION FOR SEQ ID NO:13:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:13:

CTAGTGTAGC TGCTGGTCCC AATG                    24

(2) INFORMATION FOR SEQ ID NO:14:

(i) SEQUENCE CHARACTERISTICS:
(A) LENGTH: 30
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:14:

CGAACCCAGA TTGTAAGACT ATTTTAAAAG              30

(2) INFORMATION FOR SEQ ID NO:15:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:15:

GGGACCAGCA GCTACACTAG                         20

(2) INFORMATION FOR SEQ ID NO:16:

(i) SEQUENCE CHARACTERISTICS:
(A) LENGTH: 19
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:16:

GTCTTACAAT CTGGGTTCG                          19

(2) INFORMATION FOR SEQ ID NO:17:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:17:

GTATTGCTAC TTGTGATTGC TCCA                    24

(2) INFORMATION FOR SEQ ID NO:18:

(i) SEQUENCE CHARACTERISTICS:
(A) LENGTH: 28
(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO:18:

GAGCAGTATC TGGAGACCTG GAAAAACA          28

(2) INFORMATION FOR SEQ ID NO:19:

(i) SEQUENCE CHARACTERISTICS:
        (A) LENGTH: 21
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO:19:

AGCAATCACA AGTAGCAATA C          21

(2) INFORMATION FOR SEQ ID NO:20:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO:20:

AGGTCTCCAG ATACTGCTC          19

(2) INFORMATION FOR SEQ ID NO:21:

(i) SEQUENCE CHARACTERISTICS:
        (A) LENGTH: 25
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO:21:

AGATTTTTAA ATGGCTCTTG ATAAA          25

(2) INFORMATION FOR SEQ ID NO:22:

(i) SEQUENCE CHARACTERISTICS:
        (A) LENGTH: 29
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO:22:

GCAGGGGCAA GGCCAATGGA CATATCAAA          29

(2) INFORMATION FOR SEQ ID NO:23:

(i) SEQUENCE CHARACTERISTICS:
        (A) LENGTH: 20
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO:23:

CAAGAGCCAT TTAAAAATCT                                                    20

( 2 ) INFORMATION FOR SEQ ID NO:24:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:24:

CCATTGGCCT TGCCCCTGC                                                     19

( 2 ) INFORMATION FOR SEQ ID NO:25:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:25:

TCGCAAGCAC CCTATCAGGC AGT                                                23

( 2 ) INFORMATION FOR SEQ ID NO:26:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:26:

CGAGTAGTGT TGGGTTGCGA AAGGCCTTGT GGT                                     33

( 2 ) INFORMATION FOR SEQ ID NO:27:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:27:

TGCCTGATAG GGTGCTTGCG AG                                                 22

( 2 ) INFORMATION FOR SEQ ID NO:28:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:28:

TTTCGCAACC CAACACTACT CGG                                                23

( 2 ) INFORMATION FOR SEQ ID NO:29:

( i ) SEQUENCE CHARACTERISTICS:
    ( A ) LENGTH: 53
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:29:

GGAAUUGCCA GGACGACCGG GUCCUUUCUU GGAUCAACCC GCUCAAUGCC UGG    53

( 2 ) INFORMATION FOR SEQ ID NO:30:

( i ) SEQUENCE CHARACTERISTICS:
    ( A ) LENGTH: 51
    ( B ) TYPE: nucleic acid
    ( C ) STRANDEDNESS: double
    ( D ) TOPOLOGY: linear ( i i ) MOLECULE TYPE: Other nucleic acid (synthetic DNA)

( x i ) SEQUENCE DESCRIPTION: SEQ ID NO:30:

AATTGCCACG ACGACCGGGT CCTTCTTGG ATCAACCCGC TCAATGCCTG G    51

( 2 ) INFORMATION FOR SEQ ID NO:31:

( i ) SEQUENCE CHARACTERISTICS:
    ( A ) LENGTH: 51
    ( B ) TYPE: nucleic acid
    ( C ) STRANDEDNESS: double
    ( D ) TOPOLOGY: linear ( i i ) MOLECULE TYPE: Other nucleic acid (synthetic DNA)

( x i ) SEQUENCE DESCRIPTION: SEQ ID NO:31:

CACCATAGAT CACTCCCCTG TGAGGAACTA CTGTCTTCAC GCAGAAACGG T    51

( 2 ) INFORMATION FOR SEQ ID NO:32:

( i ) SEQUENCE CHARACTERISTICS:
    ( A ) LENGTH: 53
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:32:

GGCAAGGUGA AUGUGGAAGA AGUUGGUGGU GAGGCCCUGG GCAGGCUGCU GGU    53

( 2 ) INFORMATION FOR SEQ ID NO:33:

( i ) SEQUENCE CHARACTERISTICS:
    ( A ) LENGTH: 54
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:33:

CGAACCCAGA UUGUAAGACU AUUUUAAAAG CAUUGGGACC AGCAGCUACA CUAG    54

( 2 ) INFORMATION FOR SEQ ID NO:34:

( i ) SEQUENCE CHARACTERISTICS:
    ( A ) LENGTH: 52
    ( B ) TYPE: nucleic acid
    ( C ) STRANDEDNESS: single
    ( D ) TOPOLOGY: linear -continued (i i) MOLECULE TYPE: RNA (x i) SEQUENCE DESCRIPTION: SEQ ID NO:34:

GAGCAGUAUC UGGAGACCUG GAAAAACAUG GAGCAAUCAC AAGUAGCAAU AC    52

(2) INFORMATION FOR SEQ ID NO:35:

(i) SEQUENCE CHARACTERISTICS:
  (A) LENGTH: 54
  (B) TYPE: nucleic acid
  (C) STRANDEDNESS: single
  (D) TOPOLOGY: linear (i i) MOLECULE TYPE: RNA (x i) SEQUENCE DESCRIPTION: SEQ ID NO:35:

GCAGGGGCAA GGCCAAUGGA CAUAUCAAAU UUAUCAAGAG CCAUUUAAAA AUCU    54

(2) INFORMATION FOR SEQ ID NO:36:

(i) SEQUENCE CHARACTERISTICS:
  (A) LENGTH: 57
  (B) TYPE: nucleic acid
  (C) STRANDEDNESS: single
  (D) TOPOLOGY: linear (i i) MOLECULE TYPE: RNA (x i) SEQUENCE DESCRIPTION: SEQ ID NO:36:

CGAGUAGUGU UGGGUUGCGA AAGGCCUUGU GGUACUGCCU GAUAGGGUGC UUGCGAG    57

AMPLIFICATION OF RNA SEQUENCES USING THE LIGASE CHAIN REACTION

This application is a 371 of PCT/US93/04863, filed May 24, 1993, and a continuation-in-part of U.S. application Ser. No. 07/891,543 filed May 29, 1992, now abandoned, the whole of which is incorporated by reference.

TECHNICAL FIELD

The present invention relates to methods and kits for amplifying and detecting specific RNA sequences. In particular, the invention relates to methods for producing complementary DNA (cDNA) by reverse transcription of RNA, and amplification of the DNA sequences. The analysis of the amplified material facilitates the detection of pathogens and disease states associated with the presence of particular nucleic acid sequences, so the present invention is important in medical diagnostic procedures.

BACKGROUND

Nucleic acid amplification techniques are established as powerful tools for detecting small amounts of DNA or RNA which previously were undetectable by standard nucleic acid hybridization methods. DNA amplification most commonly employs the polymerase chain reaction (PCR) as described in U.S. Pat. Nos. 4,683,195 and 4,683,202 or the ligase chain reaction (LCR) as described in EP-A-320 308 and EP-A-439 182. The entire disclosure of each of these publications is incorporated herein by reference.

When coupled with reverse transcription, PCR permits the amplification and detection of minute amounts of RNA as described in PCR Protocols: A Guide to Methods and Amplifications, Academic Press, Inc., (1990). The PCR process is discussed further in WO 91/0994, which describes a one-enzyme system that can amplify RNA. A thermostable DNA polymerase having reverse transcriptase activity is reported. The reverse transcriptase activity makes a cDNA copy of the RNA and the cDNA is amplified by PCR, using the same enzyme and reagents.

Efforts to avoid amplifying contaminating DNA are disclosed by Shuldiner et al., in published U.S. patent application Ser. No. 07/504,591 (NTIS) published May 14, 1991 for RNA template-specific PCR.

The present invention provides a method to amplify RNA using the LCR. It utilizes a combination of oligonucleotide probes and amplification methods which enhance the sensitivity and reliability of RNA amplification and detection with LCR.

SUMMARY OF THE INVENTION

The present invention relates to methods and kits useful for amplifying and detecting ribonucleic acid (RNA) from a multitude of sources. In a first aspect, the invention provides a method of amplifying a known RNA target sequence present in a biological sample, said method comprising:
  (a) treating RNA in the sample under hybridizing conditions with a first oligonucleotide probe which is hybridizable to a first segment of the known target RNA;
  (b) extending a 3' terminus of said first probe by reverse transcription of the RNA target so that a cDNA segment is produced having at its 5' end said first probe and at its extended 3' end a nucleotide sequence complementary to a second segment of the target RNA, said reverse transcription being limited to the addition of not more than about 30 nucleotides;
  (c) dissociating the extended first probe from the RNA target;
  (d) hybridizing a second oligonucleotide probe to said extended first probe, said second probe having a 3' end hybridizable to the extended cDNA segment of the first probe, but substantially not hybridizable to said first probe when it is unextended;
  (e) forming at least one of:
    (i) an elongated second probe complex by covalently ligating a third DNA probe to the 3' terminus of said second probe, with the proviso that if said second or third probe is modified, it is corrected prior to ligation of the third probe to the second probe; and
    (ii) an elongated first probe complex by forming a fourth DNA segment covalently attached to the 3' terminus of said first probe and complementary to said second probe; and
  (f) amplifying at least one of said elongated second probe complex and said elongated first probe complex.

Preferably, the length of the cDNA extension of the first probe is limited to a predetermined length by providing a pool of less than all four nucleoside triphosphate types. In this way, extension is terminated at the stopbase which calls for an omitted nucleotide.

An important part of this invention is the formation of a DNA copy from the RNA that is long enough to support amplification. The method of the invention provides several ways of accomplishing this, it being particularly important that the second probe hybridize with the first probe substantially only when the first probe has been extended on the RNA target. Ideally, the second and extended first probes hybridize together for only a relatively short portion at their respective 3' ends, leaving relatively large 5' overhangs. The 5' overhangs are then used to complete the formation of a full length DNA product. This is done by 1) polymerization extension of the second (or first) probe using the first (or second) probe as template; or 2) by ligating third or fourth probes (complementary to the 5' overhang portions of the first and second probes, respectively) to the second or first probes, respectively.

Once the full length DNA copy is made, it may be amplified by several techniques, the most useful being LCR using the same four probes mentioned already. Thus, the method further comprises amplifying by at least one repeated cycle of forming both:
  (i) an elongation complex of a third oligonucleotide probe covalently ligated to the 3' terminus of said second probe and complementary to at least a portion of said first probe, with the proviso that if said second or third probe is modified, it is corrected prior to ligation of the third probe to the second probe; and
  (ii) an elongation oligonucleotide complex covalently attached to the 3' terminus of said first probe and complementary to at least a portion of said second probe.

In a second aspect, the invention provides a method of forming cDNA of a predetermined length from a known RNA target sequence present in a sample, comprising the steps of:
  (a) treating RNA under hybridizing conditions with a first oligonucleotide probe which is hybridizable to a first segment of the target RNA; and
  (b) extending a 3' terminus of said probe by reverse transcription of the RNA under conditions including less than all four nucleoside triphosphate types, so that a cDNA segment of a predetermined length is produced, wherein such extension is terminated at said predetermined length when said RNA template requires a nucleoside triphosphate which is not present.

In a final aspect, the invention provides a diagnostic kit for detecting an RNA target present in a biological sample, comprising in combination:

(a) a first oligonucleotide probe which is complementary to a portion of the RNA target;

(b) an extending reagent capable of reverse transcription of the RNA target in the presence of a supply of the nucleoside triphosphates complementary to the RNA target region 3' of the first probe, using the first probe as a primer;

(c) a second oligonucleotide probe capable of hybridizing to said first oligonucleotide probe substantially only when said first probe has been extended by reverse transcription;

(d) at least one of
   (i) a third oligonucleotide probe complementary to a portion of said first probe, said probe having a 5' terminus ligatable to the 3' terminus of said second probe and complementary to a portion of said first probe, with the proviso that if said second or third probe is corrected prior to ligation, the second probe is ligatable to the third probe in their corrected form, thereby to form an elongated second probe complex; or
   (ii) a fourth oligonucleotide probe which is covalently ligatable to the 3' terminus of said first probe once it is extended, and complementary to a portion of said second probe, thereby to form an elongated first probe complex; and (e) an assembling reagent for forming the elongated second probe complex, the elongated first probe complex, or both.

DESCRIPTION OF THE DRAWINGS

FIG. 2 is a graphic representation of the RNA amplification method employing hepatitis C virus as the RNA target sample, as described in Example 2. The 6:2 gap and probes are shown as aligned on target. Filled portions (C and T) are shown underlined in the target and final full length DNA products; they are shown in lower case letters in the remaining frames.

DETAILED DESCRIPTION

Definitions

Figure 1:
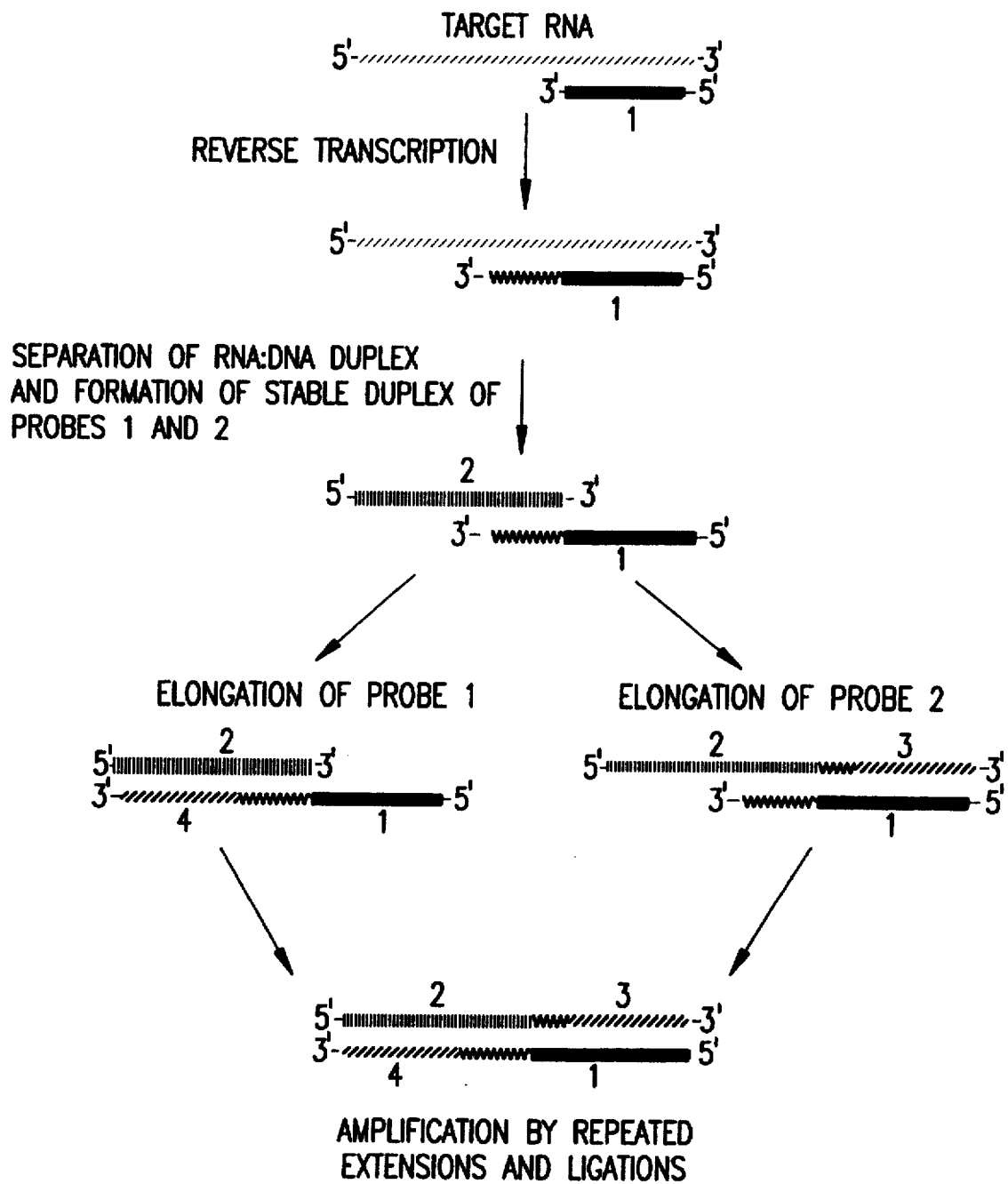
FIG. 1 is a schematic representation of the generalized RNA amplification method employing elongated first and second oligonucleotide probes. In this Figure, elongation is depicted by "squiggle" lines to represent extensions, and "shaded" bars to represent ligatable probes 3 and 4.

"Oligonucleotide" refers to a molecule consisting of two or more deoxyribonucleotides, preferably more than three. The exact size depends on many factors such as the ultimate function or use of the oligonucleotide. By definition, an oligonucleotide (sometimes shortened to "oligo") has polarity and 3' and 5' ends. As used herein, "terminus" refers to the endpoint of an oligonucleotide. Usually this is a 5' phosphate or a 3' hydroxyl, but in some cases the termini are modified, either to prevent unwanted target-independent ligation (e.g. with internal termini), or to attach a label or reporter group (e.g. external termini). By contrast, the "end" of an oligonucleotide refers to a terminal portion or segment, not the actual terminus. Typically, an oligonucleotide is a 2'-deoxyribo-oligonucleotide, but it may also be a mixed ribo/deoxyribo-oligonucleotide.

A "probe" is an oligonucleotide. The exact length of the probe according to the invention depends on many factors, including temperature, source of probe, and how it is used in the method. Probes as short as 6 or 7 nucleotides (hence the commonly used terminology "6–7 mer") and as long as several hundred-mers have been used for other purposes, but more typically probes for LCR are in the range of 10 to 40 or 50-mers. For example, depending on the complexity of the target RNA sequence, a probe typically contains 15–40 nucleotides, although it may contain more or fewer nucleotides. Probes may be derived from a natural source, as in a purified restriction digest. Alternatively, it is a routine matter to synthesize the desired probes using conventional nucleotide phosphoramidite (or phosphonate) chemistry and instruments available from Applied Biosystems, Inc., (Foster City, Calif.); DuPont, (Wilmington, Del.); or Milligen, (Bedford, Mass.). Phosphorylation of the 5' termini of the probes, which is necessary for ligation by ligase, may be accomplished by a kinase or by chemical synthesis (e.g. Phosphate-On™, Clontech, Palo Alto, Calif.) as is known in the art.

As described below, a probe is capable of acting as a point of ligation to second probe or as a point of initiation of polymerization extension (e.g. a primer). When used as a primer, the probe must be sufficiently long to permit the synthesis of extension products in the presence of a polymerization agent. "Polymerization" and "extension" refer to the addition, one by one, of nucleoside triphosphate monomers to a primer using a template as is well known in the art. By contrast, "elongation" refers to a process which results in a covalently attached longer probe regardless of the mechanism. Specifically, elongation includes the ligation of another short oligonucleotide to form an "elongation" product or complex. Elongation also encompasses a "correction" (e.g. an extension) step prior to a ligation step as is known from the incorporated The terms "modified" and "corrected", with regard to probes, have the meanings specified in U.S. Ser. No. 07/634,771 filed Jan. 9, 1991 (published as EP-A-439 182) and U.S. Ser. No. 07/925,402 filed Aug. 3, 1992, each of which is incorporated herein by reference. Briefly, a modified probe is one that cannot be ligated to its same-sense partner probe because it fails to present the proper substrate for ligase. Ligase requires the following as substrate: 1) adjacent or abutting probes, presenting 2) a 5' phosphate terminus and 3) a 3' hydroxyl terminus. Ligase exhibits a marked preference for probes meeting these requirement when they are hybridized to a template which dictates adjacency. Generally, a probe is modified by leaving a gap, an overlap (to destroy the adjacency requirement); by changing the 3' hydroxyl to a phosphate, ribonucleotide or other blocking moiety; or by altering the 5' phosphate or inserting a 5' mismatch. Other "modifications" that fall within the general definition are also contemplated by the present invention. As is described in detail in the above-noted U.S. Ser. Nos. 07/634,771 and 07/925,402, the modifications are "corrected" in template-dependent fashion to yield ligatable probes; but this correction process takes place substantially only when the probes are hybridized to target (or amplicons made from target).

It is also to be understood that the term "all 4 nucleoside triphosphate types" shall refer to Guanine (G), Cytosine (C), Adenine (A) and Thymine (T) when the context is that of DNA; or Guanine (G), Cytosine (C), Adenine (A) and Uracil (U) in the context of RNA. The term also includes analogs and derivatives of the bases named above. Accordingly, "less than all four nucleoside triphosphate types" refers to an omission of at least one of the four nucleoside triphosphates.

Method Phases

In general, the amplification method of the invention proceeds in three stages or phases: I) initial hybridization and reverse transcription; II) separation and formation of at least one strand of full length DNA; and III) amplification of the full length DNA strand(s). Division of the method into phases is not rigid however, and is intended to facilitate discussion, not to limit the invention.

In the first phase, a first probe hybridizes with target RNA if present in the sample, and is extended by reverse transcription using the RNA as template. This extension may proceed with reverse transcriptase or, under certain conditions, with DNA polymerase. For DNA polymerases tested by applicants, the presence of a divalent cation is required, typically at a concentration of about 0.5 mM to about 30 mM. It is presently believed that manganese is necessary for the reverse transcription activity of known DNA polymerases; a concentration of 0.5 mM to about 5 mM is suitable.

This initial extension to make cDNA is preferably limited so that no more than about 30 nucleotides are added to the first probe. Extension may include all four nucleotide triphosphates, as is conventional in the art for PCR amplification of RNA, but more preferably, it include less than all four nucleoside triphosphate types since cDNA of a predetermined length is usually desired. By limiting the reagents so that less than all four nucleoside triphosphate types are present, extension will cease when the RNA template dictates that an omitted nucleoside triphosphate be added to the growing primer. In this situation, the template base which calls for the addition of an omitted base is referred to herein as a "stopbase".

While a single round of first phase cDNA extension is generally sufficient to support subsequent amplification, it may be desirable to cycle the first phase to make additional cDNA copies from each RNA target molecule. Cycling requires the application of sufficient heat (or otherwise altering the stringency conditions) to separate the RNA:DNA duplexes. This is followed by cooling, to reanneal unextended first probes to the RNA target molecules, and extending the first probes again. Cycling the first phase requires that the reverse transcription activity be relatively thermostable, or that precise stringency conditions be used so as to permit separation of the RNA:DNA duplex without loss of the enzyme activity, or that the enzyme be re-added at each cycle. A polymerase enzyme having thermoactive reverse transcriptase activity has been reported by Gelland, et al. in WO 91/09944. The first phase is completed by separating the RNA:DNA duplex, usually by heating. By heating to about 100° C., the reverse transcriptase enzyme can also destroyed.

In the second phase, the extended first probe is combined with one or more other probes to synthesize at least one strand of full length DNA. A "full length" DNA strand is one which is long enough to support further amplification, typically by LCR. It can range from about 40 to over 100 nucleotides in length, usually from 40 to 60. Although it is only necessary to synthesize one full length strand, the preferred method utilizes three additional probes and synthesizes both full length strands. These same four probes are then used for a further LCR amplification phase.

In the simplest case, a full length strand of DNA is made by using all four nucleoside triphosphate types in the extension reaction. In this case, extension is not limited to a predetermined length by a stopbase, and phases I and II merge.

According to the present invention, extension is limited to a predetermined length not exceeding about 30 nucleotides. For targets, probe designs and fill criteria that permit it, a full length DNA can be made using only extension, even if less than all four nucleoside triphosphate types are used. More usually, a full length DNA is made using additional probes which can be ligated to form elongation complexes, a process which can take place by several mechanisms. In all cases a second probe is utilized under conditions such that it hybridizes to the extended first probe, but does not hybridize to the unextended first probe under the conditions used. More specifically, the 3' end of the second probe is complementary to some or all of the extended portion of the first probe. This complementary region is referred to herein as the "overlap" region, and it must be long enough for the first and second probes to form a stable hybridization complex under the reaction conditions. Its exact length is dependent on the stringency conditions (particularly temperature) and on the specific probe configurations. For example, at 25° C. an overlap of about 5–15 nucleotides is sufficient and preferred. At higher temperatures, a longer overlap region is required, and at cooler temperatures a shorter overlap may be used. The overlap length is also dependent on target constraints as is discussed in detail in the section titled "Probe Design", below.

Once a stable duplex of first and second probes is formed, one or the other (and preferably both) is filled in using the other as a template to synthesize a full length DNA (and for subsequent amplification). Several mechanisms are possible and are summarized in Table 1 below:

TABLE 1

| | |
|---|---|
| Extension of first probe | Whether or not reverse transcription was limited in the first phase, all four nucleoside triphosphate types may be added in the second phase to make an elongated first probe complex by polymerization using the second probe as template |
| Extension of second probe | All four nucleoside triphosphate types may be added in the second phase to make an elongated second probe complex by polymerization using the first probe as template |
| Elongation of first probe | Where reverse transcription was limited in the first phase, an elongated first probe complex can be formed by ligating a fourth probe to the 3' terminus of the extended first probe. While possible, in the amplification phase, to use a fourth probe which is directly ligatable to the 3' terminus of the first probe, it is preferred to use a fourth probe that is ligated to the 3' terminus of the extended first probe, and to perform extension in the second phase also. |
| Elongation of second probe | Where reverse transcription was limited in the first phase, an elongated second probe complex can be formed by ligating a third probe to the 3' terminus of the second probe. It is possible to use a third probe which is directly ligatable to the 3' terminus of the second probe. Optionally, the 3' terminus of the second probe may be "corrected", such as by extension or cleavage of a blocking moiety, prior to ligation to the third probe; or the third probe may be "corrected", such as by exonuclease cleavage of a 5' mismatched base or a 5' non-phosphate. |

It is reiterated that the modifications and corrections mentioned in this summary table are like those discussed in EP-A-439 182, and in copending U.S. Ser. No. 07/925,402, and they need not be discussed in detail here. In the preferred four probe-double gap filling version, elongation complexes are made in both the top and bottom strands by gap filling-extension and ligation. The lengths of the two gaps are preferably different; the length of the gap between first and fourth probes being about 5–15 bases, so that a stable duplex can be formed between the extended first probe and the second probe. By contrast, the gap between the second and third probes, when present, is typically much smaller, for example, from 1 to about 5–10 bases, usually defining an "asymmetric" gap. The second gap may be non-existent, which amounts to direct or abutting alignment of second and third probes. Gaps between probes that form elongation complexes may be characterized then by a gap ratio: a first number specifying the length of the gap between first and fourth probes (bottom strand), and a second number specifying the length of the gap between second and third probes (top strand). Thus, embodiments according to the invention include, but are not limited to, probe configurations having gap ratios like: 15:0 or 5:5 and several intermediate ratios, for example, 10:2, 12:3, 8:0, 8:1 or 9:3.

Although these methods may seem burdensome at first for creating full length cDNA, their true utility is seen in the amplification phase (phase III), where the same probes and nucleotide reagents that were used to create the full length DNA in the first place, are now used to amplify it.

Amplification Phase

It is possible, once the stable duplex of first and second probes is formed, to simply extend each over the other to obtain amplified DNA. This is similar to a PCR reaction, depending on the exact probe configuration. In most cases, however, first and second probes will be selected with 3' ends so that they are slightly overlapping, or essentially vertically aligned. For simple extension amplification, a polymerase is used, preferably a thermostable DNA polymerase. Several publications have described suitable thermostable polymerases, including U.S. Pat. Nos. 4,889,818 and 5,079,352, and published applications WO 91/09950 and WO 92/03556.

It is preferred, however, to synthesize at least one elongation complex by ligation of a third or fourth probe. In this case, amplification proceeds much like the LCR or the modified ends LCR described in BP-A-439 182. Of course it is possible, and within the scope of this invention, to utilize a hybrid amplification scheme, performing an extension reaction on one strand and an elongation/ligation reaction (optionally, modified and corrected) on the other strand. Hybrid amplification is less preferred when it requires additional reagents (e.g. endonuclease IV or ribonuclease).

The conditions and reagents which make possible the preferred enzymatic ligation step are generally known to those of ordinary skill in the art and are disclosed in the references mentioned in the background. Ligating reagents useful in the present invention include prokaryotic ligases such as *E coli* ligase, T4 ligase and *Thermus thermophilus* ligase (e.g., ATCC 27634) as taught in EP-320 308. This latter ligase is presently preferred for its ability to maintain activity during the thermal cycling of LCR. Other suitable thermally stable ligases are commercially available from New England Biolabs, Inc. (Beverly, Mass.), Epicentre Technologies, Inc.(Madison, Wis.) and Molecular Biology Resources (Milwaukee, Wis.). Absent a thermally stable ligase, the ligase must be added again each time the cycle is repeated. Also useful are eukaryotic ligases, including DNA ligase of Drosophilia, reported by Rabin, et al., *J. Biol. Chem.* 261:10637–10647 (1986).

Once ligated, the fused probe is dissociated (e.g. melted) from the target and, as with conventional LCR, the process is repeated for several cycles. The number of repeat cycles may vary from 1 to about 100, although from about 15 to about 70 are preferred presently.

Probe Design

For purposes of this invention, the target RNA may be any RNA selected from viral, nuclear or cytoplasmic sources including, for example, genomic RNA, mRNA, tRNA, hnRNA and rRNA, and any combination thereof.

The probes used herein are selected to be substantially complementary to the different strands of each specific sequence to be amplified. The term "selected" in this context is taken to mean that a target sequence having the desired characteristics is located and probes are constructed around an appropriate segment(s) of the target sequence. It will be understood that those of ordinary skill in the art will know how to search for and identify specific target sequences meeting the requirements of this invention. For example, many databases contain sequence information (e.g. GENBANK, NBRF, EMBL or Swiss-Prot) which can be searched by readily available computer software (e.g. MacVector, MacMolly or Geneworks). For convenience an RNA sequence in the database may readily be converted to its corresponding DNA sequence for searching using DNA search criteria, e.g. as described in Example 3. It will also be realized that in any organism's known genome, multiple locations meeting the requirements will generally be found. For example, a search of the HCV genome [GENBANK Acc. No. M58335; (see Examples 1–2, and Appendix A)], which contains approximately 9.4 kilobases, reveals over 1486 possible locations potentially suitable for practicing this invention.

Probes #1 and #3 need not reflect the exact sequence (or complement) of the template, but must be sufficiently complementary to hybridize with sequences of the target. Probe #2 need be complementary to the extended portion of probe #1 and can even overlap Probe #1, provided it does not substantially hybridize thereto prior to extension of probe #1. The remaining 5' portion of probe #2 may be any sequence at all and need not be specific for the target. Probe #4, when used, need only be complementary to the 5' potion of probe #2. Once the elongated first or second probe complexes are formed, the probes will typically be perfect complements, regardless of whether or not the original target was.

One possible exception to perfect complementarity could be the creation of a stopbase in the DNA amplification phase that was non-existent in the initial cDNA extension phase. This might be done, for example, by designing probe #2 to include a mismatch in the region of overlap between probes #1 and #2. The mismatched base calls for a dNTP not provided in the pool, whereas the original template called for a dNTP that is provided. This has the effect of permitting a longer cDNA extension product while limiting the gap fill in amplification to a smaller size. A disadvantage would be the destabilizing effect of the mismatch in the overlapping area of extended probe #1 and probe #2.

Although more detailed examples of probe design are provided at the end of the specification, a typical example will now be described. This example illustrates the identification of one type of potential 9:3 asymmetric gap LCR site that has on the top strand one base (G) followed by a 9 base sequence of T or C followed by a 3 base sequence of G or A followed by one base (T); (that is, a search is conducted for the sequence RYYYYYYYYYRRRY, wherein R=A or G and Y=C or T). Such a typical example is demonstrated by sequences found in the Hepatitis C 5' untranslated region, virus core, matrix, envelope and nonstructural protein RNA (Takamizawa,A.,et al., *J. Virology* 65:1105–1113 (1991), designated "CHUMR").

|  | SEQ ID No. |
|---|---|
| 5'-AAUUGCCAGGACGACCGGGUCCUUUCUUGGAUCAACCCGCUCAAUGCCUGG-3' | 29 |
| CCTAGTTGGGCGAGTTACGGACC-5' | 1 |
| 3'-TTAACGGTCCTGCTGGCCC | 4 |
| 5'-AATTGCCAGGACGACCGGGTCCTTTCTT | 2 |
| TCAACCCGCTCAATGCCTGG-3' | 3 |

Probes 2 and 4 are chosen such that a sufficient number of complementary bases exist between the two probes to result in a thermal melt temperature (Tm) of approximately 50°–80° C. This is usually 15–30 bases of complementarity. Similarly, probes 1 and 3 are typically chosen to have a Tm that is close to that of probes 2 and 4. In the example above, probes 2 and 4 have 19 complementary bases and probes 1 and 3 have 20 complementary bases. Probe 2 has a string of 9 bases (5'TCCTTTCTT 3') that do not hybridize with probe 4, but which serve as a template for the addition of G and A to probe 1 (by DNA polymerase, after probes 2 and 3 are ligated) during the amplification phase of the reaction. Probe 1 has a string of three bases (5'TCC 3') that do not hybridize to probe 3 but serve as template for the addition G and A to probe 2 (by DNA polymerase, with or without ligation of extended probe 1 to probe 4) during phases II or III of the reaction.

Additionally, it should be noted that the initial extension of probe 1 by reverse transcription results in an extended first probe having a predetermined length if the nucleoside triphosphate C is unavailable to the reverse transcriptase (i.e. the corresponding G on the RNA target strand serves as a stopbase). The predetermined length is the sum of original probe 1 plus the 9 added As and Gs. This 9 base added section provides an overlap between probes 1 and 2 that is sufficient to form a duplex at about 25° C. Thus, a full length DNA can be formed on the bottom strand by adding probe 4 and ligating it to extended probe 1; and full length DNA can be formed on the top strand by adding probe 3, extending probe 2, and ligating extended probe 2 to probe 3.

For the amplification phase, the probes are added in approximately equimolar concentration since they are expected to react stoichiometrically. Each probe is present in a concentration ranging from about 0.5 nanomolar (nM) to about 1000 nM; preferably from about 1 nM to about 100 nM for LCR. The optimum quantity of probe used for each reaction also varies depending on the number of cycles which must be performed. Other probe designs and optimum concentrations can readily be determined by one of ordinary skill in this art.

Another facet of probe design is related to the particular amplification method employed. If a method is used which requires only polymerization extension of probes to make elongated probe complexes, then only two probes would be required. If, on the other hand, any part of the first or second elongation probe complex is formed by ligation, one or two additional probes are needed. Thus, the invention describes three embodiments: a two probe version, a three probe version and a four probe version. In the three probe version, it is simpler if the first probe elongation product is formed by extension, while the second probe elongation complex is formed by ligation, with or without a correction mechanism (e.g. extension). In the four probe version, both elongation complexes require ligation; correction is optional, though preferred.

It should be mentioned that probes capable of detecting RNA targets may very well also be capable of detecting corresponding DNA targets of the same organism, and vice versa.

Detection

Following amplification, the amplified sequences can be detected by a number of conventional ways known in the art. No particular detection mechanism is essential to the present invention. In a particularly preferred mechanism, hooks are attached at the available outside ends of at least two probes (opposite ends of elongated probe complexes), and preferably to the outside ends of all four probes. A "hook" is any moiety having a specific ligand-receptor affinity. Typically, the hook(s) at one end comprises an antigen or hapten capable of being immobilized by a reagent (such as antibody or avidin) coated onto a solid phase. The hook(s) at the other end contains a different antigen or hapten capable of being recognized by a label or a label system such as an antibody-enzyme conjugate. Using this approach, the amplified product can be detected in any sandwich immunoassay format. A substrate is then added which is converted by the enzyme to a detectable product.

Many different haptens are known in the art, and virtually any hapten can be used with the present invention. Some illustrative haptens include many drugs (e.g.. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned patent applications U.S. Pat. Nos. 07/808,508 (adamantaneacetic acids), and 07/808,839 (carbazoles and dibenzofurans), both filed Dec. 17, 1991;U.S. Pat. Nos. 07/858,929 (acridines), and 07/858,820 (quinolines), both filed Mar. 27, 1992; and continuations-in-part of each of these four applications fled respectively on Apr. 21, 1993, , Jul. 1, 1993, Mar. 26, 1993, and Mar. 26, 1993, respectively (collectively referred to herein as the "hapten applications"). The entire disclosure of each of the above-mentioned-previously filed hapten applications is incorporated herein by reference.

Many methods of adding haptens to probes are known in the literature. Enzo Biochemical (New York) and Clontech (Palo Alto) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 and 630,908, filed Dec. 20, 1990 teach methods for labeling probes at their 5' and 3' termini respectively. Both the aforementioned copending applications are incorporated by reference.

Publications WO92/10505, published 25 Jun. 1992 and WO 92/11388 published 9 Jul. 1992 teach methods for labeling probes at their 5' and 3' ends respectively. According to one known method for labeling an oligonucleotide, a label-phosphoramidite reagent is prepared and used to add the label to the oligonucleotide during its synthesis. For example, see Thuong, N. T. et at., *Tet. Letters*, 29(46) :5905–5908 (1988); or Cohen, J. S. et al., U.S. patent application Ser. No. 07/246,688 (NTIS ORDER No. PAT-APPL-7-246.688) (1989).

Of course, other detection mechanisms, such as specific probe capture and/or detection, are also useful with the invention.

Those skilled in the art recognize that the present method can be used in a variety of contexts where amplification of RNA is desired. The following examples are provided merely to illustrate the invention and not to limit the scope of the accompanying claims. Probes are generally written in the 5' to 3' sense left to right, as is conventional; but when shown as target (or as aligned on target), one strand (or two probes) are shown in reverse.

EXAMPLES

In each of the following examples the DNA ligase is a thermostable ligase purified from *Thermus thermophilus* and the thermostable polymerase is obtained from Molecular Biology Resources (MBR), Milwaukee, Wis., derived from a Thermus species. Quantities of polymerase are expressed in units, defined (e.g.., by MBR) as follows: 1 unit of enzyme equals the amount of enzyme required to incorporate 10 nanomoles total nucleotides into acid-insoluble material in 30 min at 70° C. Units of ligase enzyme are defined (internally by Abbott Laboratories) as: 1 mg of 95% purified *Thermus thermophilus* DNA ligase has a specific activity of about $1\times10^8$ units. While this is not precisely standardized and may vary by as much as 20%, optimization is within the skill of the routine practitioner.

Example 1

Detection of Hepatitis C Virus (HCV) using a 9:3 probe design

The following probe set was designed to detect HCV target RNA as the target sequence. The underlined bases become stopbases, as will be seen. The probes were synthesized using a model 380B DNA Synthesizer (Applied Biosystems, Inc., Foster City, Calif.) and were labeled with biotin (bio) and fluorescein (fl) on the respective ends using commercially available (Clontech, Palo Alto, Calif.) biotin and fluorescein phosphoramidite reagents.

| First Probe | bio-CCAGGCATTGAGCGGGTTGA<u>T</u>CC | SEQ ID No. 1 |
|---|---|---|
| Second Probe | fl-AATTGCCACGACGACCG<u>G</u>TCCTTTCTT | SEQ ID No. 2 |
| Third Probe | pTCAACCCGCTCAATGCCTGG-bio | SEQ ID No. 4 |
| Fourth Probe | pCCCGGTCGTCGTGGCAATT-fl | SEQ ID No. 4 |

RNA target was a RNA transcript of approximately 350 bases prepared by using DNA dependent RNA polymerase and HindIII linearized DNA plasmid containing a bacterial promoter upstream of a segment of a 5' untranslated region of HCV ("HCV 5'UTR"). Detection of target RNA was accomplished by a two step reaction. The first step was a reverse transcription step to extend the first probe in the presence of only dATP and dGTP and generate a 9 base sticky end of 3'-AGGAAAGAA. Reverse transcription proceeded under the following conditions:

TABLE 2

| | Final Conc. |
|---|---|
| MgCl$_2$ | 5 mM |
| PCR buffer II | 50 mM KCl |
| | 10 mM Tris pH 8.3 |
| dGTP and dATP | 50 µM each |
| Probe 1 | 0.332 µM (4 × 10$^{12}$) |
| Reverse Transcriptase | 50 units |
| RNase inhibitor | 20 units |
| RNA Target in dH2O | as desired |

The reaction was initiated by incubation at 42° C. for one hour to allow extension of the first probe. The sample was then boiled for 5 min to inactivate the reverse transcriptase and denature the RNA:DNA hybrid.

To 20 µL of the reaction mixture above, 180 µL of the following mixture was added:

TABLE 3

| | concentration/180 µL |
|---|---|
| LCR buffer | 50 mM Epps pH 7.7, 30 mM MgCl$_2$, 19.2 mM K$^+$ |
| NAD | 111 µM |
| Oligos 2, 3 and 4 | 0.111 µM (12 × 10$^{12}$) each |
| DNA Ligase | 8925 units |
| DNA Polymerase | 1 unit |

The extended first probe was then hybridized to the second and third probes. Using GAP LCR under the conditions set forth below, the second and third probes were extended by DNA polymerase and ligated. Similarly, the fourth probe and the extended first probe were ligated when hybridized to the second probe.

The following complex was formed, wherein nucleotides shown in lowercase (all g or a) result from the extension steps, and the underlined bases are stopbases.

| | | SEQ ID Nos. |
|---|---|---|
| | 2 3 | 30 |
| fl-AATTGCCACGACGACCG<u>G</u>GTCCTTTCTTggaTCAACCCGCTCAATGCCTGG-bio | | |
| fl-TTAACGGTGCTGCTGGCCC<u>a</u>ggaaagaaCCTAGTTGGGCGAGTTACGGACC-bio | | 30' |
| 4 | 1 | |

Gap LCR extension was performed by incubation at 85° C. for 90 seconds followed by 25° C. for 30 minutes. The amplification procedure was performed for 45 cycles, each cycle consisting of an 85 second incubation at 85° C., followed by a 56° C. incubation for 60 seconds.

Following amplification, the double-labeled LCR amplification products were detected in replicates via a sandwich immunoassay performed on the Abbott IMx® system with results shown in Table 4 below. The method for detection on the IMx is described in the literature.

TABLE 4

| Number of Molecules | IMx Rate (c/s/s) |
|---|---|
| H$_2$O negative control | 39.3 |
| | 25.7 |
| | 48.6 |
| 10$^4$ HCV RNA | 143.0 |
| | 153.9 |
| 10$^6$ HCV RNA | 1269.4 |
| | 1227.0 |

TABLE 4-continued

| Number of Molecules | IMx Rate (c/s/s) |
|---|---|
| 7 × 10⁷ β-globin RNA | 14.4 |
|  | 45.0 |
| 7 × 10¹⁰ β-globin RNA | 83.4 |
|  | 71.3 |

TABLE 5-continued

|  | Final concentration/80 μL |
|---|---|
| DNA Ligase (1.53E 5U/μL) | 4500 units |
| DNA Polymerase (4 U/μL) | 0.5 unit |

The following complex was formed, wherein nucleotides shown in lowercase (all c or t) result from the extension steps, and the underlined bases are stopbases.

|  |  | SEQ ID Nos. |
|---|---|---|
| 2 | 3 | 31 |
| fl-CACCATAGATCACTCCCCTGTGAGGAActACTGTCTTCACGCAGAAACGGT-bio | | |
| fl-GTGGTATCTAGTGAGGGGACActccttGATGACAGAAGTGCGTCTTTGCCA-bio | | 31' |
| 4 | 1 | |

Example 2

Detection of Hepatitis C Virus (HCV) using a 6:2 probe design

The following probe set was designed to detect HCV target RNA as the target sequence. The underlined bases become stopbases, as will be seen. The probes were synthesized and labeled as described in Example 1.

| First Probe | bio-ACCGTTTCTGCGTGAAGACAGTAG | SEQ ID No. 5 |
|---|---|---|
| Second Probe | fl-CACCATAGATCACTCCCCTGTGAGGAA | SEQ ID No. 6 |
| Third Probe | pACTGTCTTCACGCAGAAACGGT-bio | SEQ ID No. 7 |
| Fourth Probe | pACAGGGGAGTGATCTATGGTG-fl | SEQ ID No. 8 |

RNA target was the same as in example 1. Detection of target RNA was accomplished by a two step reaction as described in Example 1, above. The first step was a reverse transcription step to extend the first probe in the presence of only dCTP and dTTP and generate a 6 base sticky end of 5'-TTCCTC. Reverse transcription proceeded as described in Example 1, Step 1, except that dCTP and dTTP were substituted for dGTP and dATP. The reaction was initiated by incubation at 42° C. for fifteen minutes. The sample was then incubated at 99° C. for 5 min to inactivate the reverse transcriptase and denature the RNA:DNA hybrid. The sample was then incubated at 5° C. for 5 min.

Using GAP LCR under the conditions set forth below, the second probe was extended by DNA polymerase and ligated to the third probe. Similarly, the fourth probe and the extended first probe were ligated when hybridized to the second probe. To 20 μL of the step 1 reaction, 80 μL of the following mixture was added.

TABLE 5

|  | Final concentration/80 μL |
|---|---|
| LCR buffer | 50 mM Epps pH. 7.7, 30 mM MgCl₂, 19.2 mM K⁺ |
| NAD (10 mM) | 62.5 μM |
| Oligos 2, 3, and 4 | 0.021 μM (1 × 10¹²) each |

Gap LCR extension was performed by incubation at 85° C. for 60 seconds followed by 25° C. for 30 minutes. The amplification procedure was performed for 47 cycles, each cycle consisting of a 30 second incubation at 85° C., followed by a 64° C. incubation for 30 seconds.

Following amplification, the double hapten labeled LCR amplification products detected in triplicates via a sandwich immunoassay performed on the Abbott IMx® system with results as follows:

TABLE 6

| Number or Molecules | IMx Rate (c/s/s) |
|---|---|
| H₂O negative control | 9.0 |
|  | 8.9 |
|  | 8.5 |
| 10¹ HCV RNA | 9.2 |
|  | 9.1 |
|  | 8.8 |
| 10² HCV RNA | 8.4 |
|  | 8.6 |
|  | 8.8 |
| 10³ HCV RNA | 9.0 |
|  | 9.1 |
|  | 8.7 |
| 10⁴ HCV RNA | 1076.3 |
|  | 778.1 |
|  | 820.5 |
| 1 × 10⁷ β-globin RNA | 8.4 |
|  | 8.7 |
|  | 8.7 |

Thus, 10⁴ HCV target molecules could be distinguished from no target.

It is well understood by those skilled in the art that 100% homology is not essential to achieve hybridization. Depending on the precise conditions, as little as 60% homology may be sufficient to achieve hybridization, albeit under lower stringency conditions. For thermally cycled procedures such as LCR and PCR, homology in the range of 75–100% is thought necessary, preferably at least 80%. Thus, a 20-mer probe may vary from target in as many as 4 nucleotides. Of course, the position of any mismatches in the probe may be crucial. Mismatches at the juncture of extension or ligation, if tolerated at all, will have a much more deleterious effect than an equivalent number of mismatches at the outside ends of the probes.

Example 3

Location of HCV target regions compatible with other probe designs

The invention is useful with any known RNA target. For any DNA regions known to code for RNA (e.g. mRNA or rRNA), or for any known RNA sequences, the sequences can be searched for target regions meeting the requirements of this invention. Of course, it may be desirable to convert a RNA sequence to its corresponding DNA sequence first. A generalized search methodology is to look for regions that meet the criteria of Table 8 below, wherein the symbols have the following meanings:

TABLE 7

| Symbol | Meaning | Symbol | Meaning |
|---|---|---|---|
| A | Adenine | R | A or G only |
| B | any base but adenine (not A) | S | C or G only |
| C | Cytosine | T | Thymine |
| D | any base but cytosine (not C) | U | Uracil |
| G | Guanine | V | any base but thymine/uracil |
| H | any base but guanine (not G) | W | A or T/U only |
| K | G or T/U only | Y | C or T/U only |
| M | A or C only | | |
| N | any base | h | an integer from about 5 to about 15 |
| | | k | an integer from 0 to about 5 |

TABLE 8

EXEMPLARY ASYMMETRIC GAP TARGETS
(The dot "." serves only to align sequences in the Table and to divide between right and left probe sets:
All targets are written with their 5' end to the left.)

| | SEQUENCES TO SEARCH FOR | |
|---|---|---|
| Filling with just one nucleoside triphosphate type | V(T)$_h$. (A)$_k$B | A fills |
| | H(G)$_h$. (C)$_k$D | C fills |
| | D(C)$_h$. (G)$_k$H | G fills |
| | B(A)$_h$. (T)$_k$V | T fills |
| Filling with two complementary nucleoside triphosphate types | S(W)$_h$. (S)$_k$W | C and G fill |
| | W(S)$_h$. (W)$_k$S | A and T fill |
| Filling with two non-complementary nucleoside triphosphate types | M(K)$_h$. (M)$_k$K | A and C fill |
| | R(Y)$_h$. (R)$_k$Y | A and G fill |
| | Y(R)$_h$. (Y)$_k$R | C and T fill |
| | K(M)$_h$. (K)$_k$M | G and T fill |
| Filling with all three nucleoside triphosphate types | T(V)$_h$. (B)$_k$A | C, G and T fill |
| | G(H)$_h$. (D)$_k$C | A, G and T fill |
| | C(D)$_h$. (H)$_k$G | A, C and T fill |
| | A(B)$_h$. (V)$_k$T | A, C and G fill |

Integers are selected for h and k and the search is conducted. It may be predicted that few target regions will be found which support single nucleoside triphosphate filling. If such regions do exist, they may not work well due to melting temperature constraints or secondary structure constraints. By contrast, one might expect to find even greater numbers of locations when three different nucleoside triphosphates are used to fill the gap. To strike a balance between the number of available locations and a desire to limit the amount of reagents added to each reaction, it seems reasonable to search for regions which can be filed with two nucleotide types.

The attached Appendix A shows just such two-base-fill locations in the CHUMR HCV Sequence, using conventional nomenclature understood by those skilled in the art.

Example 4

Detection of Rabbit β-globin mRNA using a 10:1 probe design

An assay is performed for the detection of rabbit β-globin mRNA according to the procedures and conditions of Examples 1 and 2. The mRNA sequence and numbering system is that published by GENBANK, ver. 69 Acc NO. J00659 and the selected probes hybridize in the region between 532 and 584. The following probes were synthesized and labeled as described in Example 1, the stop bases being underlined:

| | | |
|---|---|---|
| First Probe | biotin-ACCAGCAGCCTGCCCAGGGCCT | SEQ ID No. 9 |
| Second Probe | fluor-GCAAGGTGAATGTGGAAGAAGTTGGTGGTG | SEQ ID No. 10 |
| Third Probe | pGGCCCTGGGCAGGCTGCTGG-biotin | SEQ ID No. 11 |
| Fourth Probe | pTTCTTCCACATTCACCTTGCC-fluor | SEQ ID No. 12 |

The probes are designed in this case to have a 10 base gap between the first and fourth probes, and a 1 base gap between the second and third probes. They align on target (SEQ ID No 32) as follows, the gaps being filled by C and A only:

| | SEQ ID Nos. |
|---|---|
| 5'-GCAAGGUGAAUGUGGAAGAAGUUGGUGGUGAGGCCCUGGGCAGGCUGCUGGU-3' | 32 |
| TCCGGGACCCGTCCGACGACCA-5' | 9 |
| 3'-CCGTTCCACTTACACCTTCTT | 12 |
| 5'-GCAAGGTGAATGTGGAAGAAGTTGGTGGTG | 10 |
| GGCCCTGGGCAGGCTGCTGGT-3' | 11 |

The outside termini of the probes are labeled with differentiable haptens biotin and fluorescein as before and the amplified product is detected in the Abbott IMx® system as before.

It is noted that two other potential asymmetric gap LCR locations have been identified in the rabbit β-globin mRNA as shown in Table 9 below. Note that the gap in the top strand is nonexistent in these cases.

TABLE 9

| Position | Gap ratio | Filling nucleotides |
|---|---|---|
| 467–477 | 11:0 | G and T |
| 1645–1653 | 9:0 | A and T |

Of course, as discussed above, one would expect to find several other locations in the genome if the search were expanded to include shorter gaps, or to include three nucleotide types in filling the gap.

Example 5

Detection of HIV RNA using a 11:4 probe design

The following probes were synthesized as described in Example 1. The probe ends indicated were labeled with reporter haptens designated "crb" (for a carbazole derivative) and "adam" (for an adamantane derivative) using hapten-phosphoramidites as is known in the art (see section above on Detection).

| Designation | 5'-Sequence-3' | Sequence ID No. |
|---|---|---|
| 1 | adam-CTAGTGTAGCTGCTGGTCCCAATG | 13 |
| 2 | crb-CGAACCCAGATTGTAAGACTATTTTAAAAG | 14 |
| 3 | pGGGACCAGCAGCTACACTAG-adam | 15 |
| 4 | pGTCTTACAATCTGGGTTCG-crb | 16 |

The probes are specific for positions 1773–1826 of the GAG region of HIV-1 and were selected from HIV SF2CG GenBank release 71 Accession number K02007. HIV RNA target was a RNA transcript of approximately 675 bases prepared as in example 1 using an insert of HIV DNA in place of the HCV DNA and linearized with EcoR1. Probes align on the target (SEQ. ID No 33) as shown below, such that only A, T and C are needed to fill. The nucleotides underlined and in lower case are deliberate mismatches introduced to relieve secondary structure; underlined nucleotides in upper case are stopbases.

| | SEQ ID Nos. |
|---|---|
| 5'-CGAACCCAGAUUGUAAGACUAUUUUAAAAGCAUUGGGACCAGCAGCUACACUAG-3' | 33 |
| GTAACCCTGGTCGTCGATGTGATC-5' adam | 13 |
| crb3' GcTTGGGTCTAACATTCTG | 16 |
| crb5' CgAACCCAGATTGTAAGACTATTTTAAAAG | 14 |
| GGGACCAGCAGCTACACTAG-3' adam | 15 |

The HIV target was diluted in 5 ng/μL of *E. coli* 16s23s ribosomal RNA and the diluent *E. coli* 16s23s ribosomal RNA alone served as a negative control.

The detection of HIV RNA was accomplished in phases. The first step was to synthesize a cDNA from the target and probe #1, providing only dATP, dCTP, and dTTP to generate an 11 base limited length extension. This creates a sticky end vs. probe #2. cDNA was formed under incubation conditions of 99° C. for 1 second, 62° C. for 15 minutes, and 4° C. for 2 minutes in the following mixture.

| | μL per reaction | Final concentration |
|---|---|---|
| Mineral Oil | — | 1 drop |
| 10 mM MnCl₂ | 1.8 | 1 mM MnCl2 |
| 100 mM Tris/900 mM KCl pH 8.3 | 1.8 | 10 mM Tris pH 8.3 90 mM KCl |
| Thermus sp. Polymerase 4 U/μL | .125 | 0.5 Units |
| dATP, dCTP & dTTP (1 mM) | 0.18 | 10 μM each |
| H₂O | 12.93 | |
| Oligo #1 1 × 10¹²/μL | 0.80 | 8 × 10¹¹ oligos |
| RNA Target | 2.0 | variable |

The second step was formation of a full length DNA product by separating extended probe 1 from the template RNA and hybridizing its sticky end with probe 2, and ligating probe 4 to extended probe 1, using probe 2 as the template. Step three, which is really done concurrently with step 2, was Gap LCR (GLCR) as described in EP-A-439 182. This process takes advantage of the sticky ended probe #1 generated in the first step. Probes 2 and 3 can now both hybridize to the extended probe #1. Probe 2 is also extended in the presence of only dATP, dCTP and dTTP and is ligated to probe #3 to form a first DNA target strand for subsequent GLCR cycles of amplification. Similarly, in subsequent cycles, probe #4 and the extended probe #1 can be ligated while hybridized to probe #2 to form a second DNA target strand for amplification.

To 20 μL of the above reaction mixture, 180 μL of the following mixture was added. The 200 μL reaction mixture was cycled 40 times at 97° C. for 1 second, 55° C. for 1 second, and 62° C. for 50 seconds.

| | per reaction | Final conc./200 μL |
|---|---|---|
| H₂O | 130.28 | — |
| LCR buffer | 40.0 | 50 mM Epps pH 7.7 |

-continued

| | per reaction | Final conc./200 μL |
|---|---|---|
| | | 18.8 mM K⁺ |
| Oligos 2, 3 & 4 | 0.8 | 8 × 10¹¹ oligos each |
| DNA Ligase | 0.0526 | 8942 Units |

-continued

|  | per reaction | Final conc./200 μL |
|---|---|---|
| Thermus sp. Polymerase | 0.125 | 0.5 Units |
| 5% EGTA/1M KOH | 1.14 | 0.75 mM EGTA |
| 1M MgCl₂ | 6.0 | 30 mM |

|  | SEQ ID Nos. |
|---|---|
| 5'-GAGCAGUAUCUGGAGACCUGGAAAAACAUGGAGCAAUCACAAGUAGCAAUAC-3' | 34 |
| ACCTCGTTAGTGTTCATCGTTATG-5' adam | 17 |
| crb3' CTCGTCATAGAcCTCTGGA | 20 |
| crb5' GAGCAGTATCTgGAGACCTGGAAAAACA | 18 |
| AGCAATCACAAGTAGCAATAC-3' adam | 19 |

Following amplification, the double hapten labeled LCR amplification products were detected in triplicates via a sandwich immunoassay performed on the Abbott IMx® system with results as follows:

TABLE 10

| Number or Molecules | IMx Rate (c/s/s) |
|---|---|
| rRNA (negative control) | 7.9 |
|  | 7.4 |
|  | 6.9 |
| 10 HIV RNA | 7.3 |
|  | 9.0 |
|  | 18.0 |
| 10² HIV RNA | 29.9 |
|  | 37.7 |
|  | 22.3 |
| 10³ HIV RNA | 105.9 |
|  | 43.6 |
|  | 141.9 |
| 10⁴ HIV RNA | 496.6 |
|  | 525.3 |
|  | 655.4 |

This shows detection sensitivity of at least $10^3$ molecules and potentially $10^2$ molecules of target HIV RNA.

Example 6

Detection of HIV RNA using a 9:3 probe design

The following probes were synthesized as described in Example 1. The probe ends indicated were labeled with reporter haptens designated "crb" (for a carbazole derivative) and "adam" (for an adamantane derivative) using hapten-phosphoramidites as in Example 5.

| Designation | 5'-Sequence-3' | Sequence ID No. |
|---|---|---|
| 1 | adam-GTATTGCTACTTGTGATTGCTCCA | 17 |
| 2 | crb-GAGCAGTATCTGGAGACCTGGAAAAACA | 18 |
| 3 | pAGCAATCACAAGTAGCAATAC-adam | 19 |
| 4 | pAGGTCTCCAGATACTGCTC-Crb | 20 |

The probes are specific for positions 8905–8956 of the NEF region of HIV-1 and were selected from HIV SF2CG GertBank release 71 Accession number K02007. HIV target was CsCl purified total cellular RNA from HIV infected H9 IIIB cells. Probes align on the target (SEQ ID No 34) as shown below, such that only G, T and C are needed to fill. The nucleotides underlined and in lower case are deliberate mismatches introduced to relieve secondary structure; underlined nucleotides in upper case are stopbases.

The HIV target was diluted in 5 ng/μL of E. coli 16s23s ribosomal RNA and the diluent E. coli 16s23s ribosomal RNA alone served as a negative control.

The detection of HIV RNA was accomplished in phases as described in example 5 except that dGTP replaced dATP for the extension steps and a 9 base limited length extension resulted, having a sticky end with respect to the second probe.

Following amplification, the double hapten labeled LCR amplification products were detected in replicates via a sandwich immunoassay performed on the Abbott IMx® system with results as follows:

TABLE 11

| Number of Molecules | IMx Rate (c/s/s) |
|---|---|
| Ribosomal RNA (Negative control) | 7.1 |
|  | 156.5 |
|  | 37.6 |
|  | 43.4 |
|  | 7.3 |
|  | 70.1 |
| approximately 10² molecules | 7.1 |
|  | 71.4 |
|  | 64.8 |
|  | 30.8 |
|  | 6.8 |
|  | 22.8 |
| approximately 10³ molecules | 272.5 |
|  | 122.4 |
|  | 190.5 |
|  | 262.8 |
|  | 279.8 |
|  | 409.2 |
| approximately 10⁴ molecules | 1163.8 |
|  | 829.7 |
|  | 1128.6 |
|  | 996.8 |
|  | 1514.9 |
|  | 1206.7 |

This shows detection sensitivity of about $10^3$ molecules of target RNA.

Example 7

Detection of HIV RNA using a 10:5 probe design

The following probes were synthesized as described in Example 1. The probe ends indicated were labeled with reporter haptens designated "crb" (for a carbazole derivative) and "adam" (for an adamantane derivative) using hapten-phosphoramidites as in Example 5.

| Desig- nation | 5'-Sequence-3' | Sequence ID No. |
|---|---|---|
| 1 | adam-AGATTTTTAAATGGCTCTTGATAAA | 21 |
| 2 | crb-GCAGGGGCAAGGCCAATGGACATATCAAA | 22 |
| 3 | PCAAGAGCCATTTAAAAATCT-adam | 23 |
| 4 | pCCATTGGCCTTGCCCCTGC-crb | 24 |

The probes are specific for positions 3549–3603 of the pol region of HIV-1 and were selected from HIV SF2CG GenBank release 71 Accession number K02007. HIV RNA target was the CsCl purified total cellular RNA preparation as in Example 6. Probes align on the target (SEQ ID No 35) as shown below, such that only dATP, dGTP, and TTP are needed to fill. Underlined nucleotides are stopbases.

| | SEQ ID Nos. |
|---|---|
| 5'-AGGGGCAAGGCCAAUGGACAUAUCAAAUUUAUCAAGAGCCAUUUAAAAAUCU-3' | 35 |
| AAATAGTTCTCGGTAAATTTTTAGA-5' adam | 21 |
| crb3' CGTCCCCGTTCCGGTTACC | 24 |
| crb5' GCAGGGGCAAGGCCAATGGACATATCAAA | 22 |
| CAAGAGCCATTTAAAAATCT-3' adam | 23 |

Extension and amplification phases were performed as in Example 5 except 1×10$^2$ of each probe was used per reaction and dATP, dTTP and dGTP (at 10 μM) were used to fill. Following amplification, the double hapten labeled LCR amplification products were detected in replicates via a sandwich immunoassay performed on the Abbott IMx® system with results as follows:

TABLE 12

| Number or Molecules | IMx Rate (c/s/s) |
|---|---|
| Negative Control | 7.2 |
| | 7.2 |
| | 7.4 |
| | 7.3 |
| | 7.0 |

TABLE 12-continued

| Number or Molecules | IMx Rate (c/s/s) |
|---|---|
| approximately 10$^3$ target molecules | 472.5 |
| | 352.5 |
| | 680.4 |
| | 208.1 |
| | 16.4 |
| | 845.8 |

Example 8

Detection of Hepatitis C Virus (HCV) using an 11:2 probe design

The following probes were synthesized as described in Example 1. The probe ends indicated and were labeled with biotin (bio) and fluorescein (fl) on the respective ends using commercially available (Clontech, Palo Alto, Calif.) biotin and fluorescein phosphoramidite reagents.

| Designation | 5'-Sequence-3' | Sequence ID No. |
|---|---|---|
| 1 | fl-TCGCAAGCACCCTATCAGGCAGT | 25 |
| 2 | bt-CGAGTAGTGTTGGGTTGCGAAAGGCCTTGTGGT | 26 |
| 3 | pTGCCTGATAGGGTGCTTGCGAG-fl | 27 |
| 4 | pTTTCGCAACCCAACACTACTCGG-bt | 28 |

The probes are specific for the 5'UTR at positions 246–302 of the HPCHUMR Sequence as found in GenBank release 71 Accession number M58335. HCV RNA target was that used in Example 1. Probes align on the target (SEQ ID No 36) as shown below, such that only A, C and G are needed to fill. Stopbases are underlined.

| | SEQ ID Nos. |
|---|---|
| 5'-CGAGUAGUGUUGGGUUGCGAAAGGCCUUGUGGUACUGCCUGAUAGGGUGCUUGCGAG-3' | 36 |
| TGACGGACTATCCCACGAACGCT-5' fl | 25 |
| bt3' GGCTCATCACAACCCAACGCTTT | 28 |

| | SEQ ID Nos. |
|---|---|
| bt5' CGAGTAGTGTTGGGTTGCGAAAGGCCTTGTGGT | 26 |
| TGCCTGATAGGGTGCTTGCGAG-3' fl | 27 |

The HCV target was diluted in 2 ng/μL of *E. coli* 16s23s ribosomal RNA and the diluent *E. coli* 16s23s ribosomal RNA alone served as a negative control.

The detection of HCV RNA was accomplished in phases. The first step was to synthesize a cDNA from the RNA target and probe #1, providing only dATP, dCTP, and dGTP to generate an 11 base limited length extension. This creates a sticky end vs. probe #2. cDNA was formed under incubation conditions of 99° C. for 1 second, 62° C. for 15 minutes, and 4° C. for 2 minutes in the following mixture.

| | μL per reaction | Final concentration |
|---|---|---|
| Mineral oil | — | 1 drop |
| 10 mM MnCl$_2$ | 1.8 | 1 mM MnCl$_2$ |
| 100 mM Tris/900 mM KCl pH 8.3 | 1.8 | 10 mM Tris pH 8.3 90 mM KCl |
| Thermus sp. Polymerase 4 U/μL | .125 | 0.5 Units |
| dATP, dCTP & dGTP | 0.18 | 10 μM (each) |
| H$_2$O | 4.93 | |
| Oligo #1 1 × 10$^{12}$/μL | 0.80 | 8 × 10$^{11}$ oligos |
| RNA Target | 2.0 | variable |

The second step was formation of a full length DNA product by separating extended probe 1 from the template RNA and hybridizing its sticky end with probe 2, and ligating probe 4 to extended probe 1, using probe 2 as the template. Step three, which is really done concurrently with step 2, was Gap LCR (GLCR) as described in EP-A-439 182. This process takes advantage of the sticky ended probe #1 generated in the first step. Probes 2 and 3 can now both hybridize to the extended probe #1. Probe 2 is also extended in the presence of only dATP, dCTP and dTTP and is ligated to probe #3 to form a first DNA target strand for subsequent GLCR cycles of amplification. Similarly, in subsequent cycles, probe #4 and the extended probe #1 can be ligated while hybridized to probe #2 to form a second DNA target strand for amplification. The following reaction mixture was cycled 40 times at 97° C. for 1 second, 55° C. for 1 second, and 62° C. for 50 seconds.

To 20 μL of the above reaction mixture, 180 μL of the following mixture was added. The 200 μL reaction mixture was cycled 40 times at 97° C. for 1 second, 55° C. for 1 second, and 62° C. for 50 seconds.

| | per reaction | Final conc./200 μL |
|---|---|---|
| H$_2$O | 130.28 | — |
| LCR buffer | 40.0 | 50 mM Epps pH 7.7 18.8 mM K$^+$ |
| Oligos 2, 3 and 4 | 0.8 | 8 × 10$^{11}$ oligos (each) |
| DNA Ligase | 0.0526 | 8942 Units |
| Thermus sp. Polymerase | 0.125 | 0.5 Units |
| 5% EGTA/1M KOH | 1.14 | 0.75 mM EGTA |
| 1M MgCl$_2$ | 6.0 | 30 mM |

Following amplification, the double hapten labeled LCR amplification products were detected in triplicates via a sandwich immunoassay performed on the Abbott IMx® system with results as follows:

TABLE 13

| Number or Molecules | IMx Rate (c/s/s) |
|---|---|
| rRNA (negative control) | 19.9 |
| | 36.5 |
| | 18.3 |
| 10$^2$ HCV RNA | 383.0 |
| | 341.2 |
| | 692.2 |
| 10$^3$ HCV RNA | 1287.4 |
| | 1215.7 |
| | 1321.7 |

This shows detection sensitivity of about 10$^2$ molecules of target HCV RNA.

The foregoing examples serve to illustrate the invention, not to limit it. The invention is defined by the appended claims.

Appendix A

Positions and Types of HCV RNA Targets Supporting Asymmetric Gap LCR
(Position numbering based on GENBANK, Acc. No. M58335)

| No. of Sites | Length and Fill Criteria | Positions | | | | | | |
|---|---|---|---|---|---|---|---|---|
| 1 | 10-0 MK | 4128 | | | | | | |
| 1 | 11-0 MK | 470 | | | | | | |
| 1 | 11-0 YR | 6066 | | | | | | |
| 1 | 8-0 SW | 8830 | | | | | | |
| 1 | 9-0 SW | 2880 | | | | | | |
| 2 | 10-0 KM | 381 | 8232 | | | | | |
| 3 | 10-0 RY | 857 | 868 | 8882 | | | | |
| 3 | 10-0 YR | 1927 | 3507 | 7134 | | | | |
| 3 | 11-0 RY | 121 | 2924 | 5999 | | | | |
| 4 | 11-0 WS | 762 | 1386 | 3378 | 5919 | | | |
| 4 | 12-0 WS | 1968 | 2036 | 3987 | 7206 | | | |
| 4 | 12-0 YR | 4499 | 7326 | 8047 | 9141 | | | |
| 5 | 9-0 RY | 190 | 3797 | 4458 | 7505 | 8139 | | |
| 6 | 11-0 KM | 369 | 2067 | 5253 | 5558 | 5745 | 9189 | |
| 6 | 7-0 SW | 1259 | 1576 | 4275 | 8015 | 8352 | 8374 | |
| 7 | 10-0 WS | 479 | 546 | 1506 | 3222 | 4203 | 5801 | 5831 |
| 7 | 6-0 SW | 688 | 935 | 6227 | 6358 | 8308 | 9183 | 9272 |
| 7 | 8-0 YR | 1503 | 2238 | 2282 | 3784 | 4822 | 7851 | 9265 |
| 7 | 9-0 MK | 260 | 2030 | 3569 | 3900 | 4246 | 6624 | 6804 |
| 8 | 9-0 YR | 363 | 4529 | 6765 | 7123 | 7514 | 7645 | 7743 |
| | | 8227 | | | | | | |
| 10 | 8-0 MK | 430 | 2053 | 2869 | 3315 | 3401 | 3519 | 4838 |
| | | 5384 | 6276 | 8850 | | | | |
| 12 | 8-0 KM | 117 | 1866 | 2120 | 2376 | 2922 | 3003 | 3533 |
| | | 6988 | 7712 | 7873 | 8639 | 9360 | | |
| 12 | 9-0 KM | 896 | 1099 | 1322 | 1582 | 1957 | 4164 | 4970 |
| | | 5201 | 5802 | 6416 | 8001 | 8657 | | |

Appendix A-continued

Positions and Types of HCV RNA Targets Supporting Asymmetric Gap LCR
(Position numbering based on GENBANK, Acc. No. M58335)

| No. of Sites | Length and Fill Criteria | Positions | | | | | | |
|---|---|---|---|---|---|---|---|---|
| 12 | 9-0 WS | 234 | 388 | 412 | 638 | 673 | 772 | 2617 |
|  |  | 3398 | 3447 | 3897 | 4798 | 4932 |  |  |
| 19 | 7-0 RY | 37 | 588 | 763 | 1213 | 2369 | 2649 | 3851 |
|  |  | 5436 | 5755 | 6997 | 7100 | 7258 | 7300 | 7493 |
|  |  | 8180 | 8693 | 8764 | 8890 | 9167 |  |  |
| 20 | 8-0 RY | 1041 | 1190 | 1632 | 2468 | 2960 | 3263 | 3541 |
|  |  | 3982 | 5085 | 5481 | 5801 | 6125 | 6179 | 6553 |
|  |  | 6700 | 6754 | 6870 | 6964 | 7439 | 8639 |  |
| 20 | 8-0 WS | 311 | 458 | 659 | 1138 | 1407 | 2052 | 2238 |
|  |  | 2922 | 3162 | 3308 | 3610 | 4258 | 4593 | 5411 |
|  |  | 6539 | 7503 | 8331 | 8432 | 8652 | 9146 |  |
| 24 | 7-0 KM | 1358 | 1666 | 1804 | 2886 | 3187 | 3436 | 3982 |
|  |  | 5134 | 5261 | 6127 | 6244 | 6455 | 6532 | 6548 |
|  |  | 6791 | 7216 | 7503 | 7944 | 7989 | 8014 | 8036 |
|  |  | 8466 | 8579 | 9077 |  |  |  |  |
| 26 | 7-0 YR | 128 | 486 | 1030 | 2052 | 2938 | 3617 | 4425 |
|  |  | 4449 | 4850 | 5011 | 5462 | 5774 | 5871 | 6209 |
|  |  | 6384 | 6397 | 7240 | 7566 | 7800 | 7963 | 8106 |
|  |  | 8402 | 8584 | 8730 | 8913 | 9374 |  |  |
| 29 | 7-0 MK | 10 | 278 | 612 | 655 | 692 | 769 | 1134 |
|  |  | 1167 | 1335 | 1503 | 1643 | 1923 | 2127 | 2590 |
|  |  | 2644 | 2912 | 3125 | 3457 | 3833 | 4495 | 5323 |
|  |  | 5374 | 5583 | 6027 | 6296 | 7265 | 8319 | 9070 |
|  |  | 9304 |  |  |  |  |  |  |
| 34 | 6-0 RY | 1146 | 1197 | 1466 | 1646 | 2703 | 2849 | 3410 |
|  |  | 3677 | 3691 | 3810 | 3826 | 3873 | 4232 | 4512 |
|  |  | 4876 | 5050 | 5957 | 5984 | 6515 | 6937 | 7027 |
|  |  | 7178 | 7219 | 7349 | 7358 | 7678 | 8025 | 8115 |
|  |  | 8158 | 8242 | 8386 | 9025 | 9329 | 9356 |  |
| 36 | 7-0 WS | 12 | 117 | 449 | 572 | 646 | 1224 | 1266 |
|  |  | 1430 | 1653 | 1846 | 2134 | 2573 | 2796 | 2943 |
|  |  | 3346 | 3416 | 3483 | 4359 | 4495 | 4904 | 4955 |
|  |  | 5348 | 5774 | 5809 | 6006 | 6109 | 6394 | 7049 |
|  |  | 7149 | 7521 | 7870 | 8064 | 8572 | 8591 | 8939 |
|  |  | 9262 |  |  |  |  |  |  |
| 41 | 6-0 YR | 45 | 66 | 269 | 314 | 515 | 769 | 811 | 835 |

| No. of Sites | Length and Fill Criteria | Positions | | | | | | | |
|---|---|---|---|---|---|---|---|---|---|
|  |  |  | 1168 | 1395 | 1432 | 1563 | 2030 | 2299 |  |
|  |  | 2581 | 2772 | 3114 | 3294 | 3392 | 3820 | 3897 |  |
|  |  | 5074 | 5405 | 5429 | 5496 | 5526 | 6268 | 6599 |  |
|  |  | 6625 | 6911 | 7041 | 7075 | 7172 | 7469 | 7522 |  |
|  |  | 7909 | 7975 | 8014 | 8300 | 8784 | 9062 |  |  |
| 45 | 6-0 KM | 23 | 200 | 391 | 523 | 532 | 633 | 661 | 669 |
|  |  |  | 762 | 920 | 1490 | 1811 | 2017 | 2080 |  |
|  |  | 2102 | 2342 | 2746 | 3628 | 3677 | 3698 | 3798 |  |
|  |  | 4014 | 4193 | 4615 | 4700 | 4711 | 4739 | 4927 |  |
|  |  | 4995 | 5032 | 5363 | 5546 | 5687 | 5790 | 6217 |  |
|  |  | 6496 | 6563 | 6873 | 6920 | 7023 | 7309 | 7690 |  |
|  |  | 8133 | 8797 | 9381 |  |  |  |  |  |
| 46 | 6-0 MK | 222 | 416 | 738 | 796 | 972 | 1009 | 1186 |  |
|  |  | 1377 | 1467 | 1742 | 1840 | 1883 | 2160 | 2289 |  |
|  |  | 2461 | 2540 | 2714 | 2845 | 3329 | 3865 | 3920 |  |
|  |  | 4177 | 4255 | 4887 | 4976 | 5113 | 5315 | 5851 |  |
|  |  | 5880 | 6053 | 6358 | 6588 | 6903 | 6912 | 7084 |  |
|  |  | 7333 | 7701 | 7894 | 7958 | 8023 | 8125 | 8295 |  |
|  |  | 8381 | 8733 | 9045 | 9154 |  |  |  |  |
| 53 | 6-0 WS | 124 | 783 | 844 | 1553 | 1923 | 2313 | 2325 |  |
|  |  | 2657 | 2690 | 2718 | 3076 | 3198 | 3619 | 3877 |  |
|  |  | 4057 | 4130 | 4546 | 4671 | 4856 | 5131 | 5194 |  |
|  |  | 5326 | 5689 | 5733 | 5839 | 5893 | 5946 | 6067 |  |
|  |  | 6154 | 6374 | 6478 | 6576 | 6585 | 6592 | 6618 |  |
|  |  | 6740 | 6920 | 7035 | 7062 | 7180 | 7297 | 7410 |  |
|  |  | 7434 | 7616 | 8380 | 8423 | 8439 | 8763 | 8840 |  |
|  |  | 9101 | 9115 | 9211 | 9222 |  |  |  |  |

What is claimed is:

1. A method of amplifying a known RNA target sequence present in a biological sample, said method comprising:
  (a) treating RNA in the sample under hybridizing conditions with a first oligonucleotide probe which is hybridizable to a first segment of the known target RNA under hybridizing conditions;
  (b) extending a 3' terminus of said first probe by reverse transcription of the RNA target so that a cDNA segment is produced having at its 5' end said first probe and at its extended 3' end a nucleotide sequence complementary to a second segment of the target RNA, said reverse transcription being limited, by a stopbase, to the addition of not more than about 30 nucleotides;
  (c) dissociating the extended first probe from the RNA target;
  (d) hybridizing a second oligonucleotide probe to said extended first probe, said second probe having a 3' end hybridizable to the extended cDNA segment of the first probe, but substantially not hybridizable to said first probe when it is unextended;
  (e) forming at least one of:
    (i) an elongated second probe complex by covalently ligating a third oligonucleotide probe to the 3' terminus of said second probe, with the proviso that if said second or third probe is modified, it is corrected prior to ligation of the third probe to the second probe; or
    (ii) an elongated first probe complex by forming a fourth oligonucleotide segment covalently attached to the 3' terminus of said extended first probe and complementary to said second probe; and
  (f) amplifying at least one of said elongated second probe complex and said elongated first probe complex.

2. The method of claim 1, wherein said elongated first probe complex is formed by the polymerization of nucleotide triphosphates to the 3' terminus of the extended first probe.

3. The method of claim 1, wherein said elongated first probe complex is formed by covalently ligating a fourth oligonucleotide probe to the 3' terminus of the extended first probe.

4. The method of claim 3, wherein said first probe is extended by polymerization of nucleotide triphosphates to its 3' end, and wherein said elongated first probe complex is formed by covalently ligating the 5' terminus of a fourth oligonucleotide probe to the 3' terminus of the extended first probe.

5. The method of claim 4, wherein said first probe is extended by polymerization of between about 5 and about 15 nucleotides.

6. The method of claim 1, wherein said elongated second probe complex is formed by covalently ligating the 5' end of a third oligonucleotide probe directly to the 3' terminus of the second probe.

7. The method of claim 1, wherein said second probe is corrected by polymerization extension, adding nucleotide triphosphates to its 3' end, and wherein said elongated second probe complex is formed by covalently ligating the 5' terminus of a third oligonucleotide probe to the 3' terminus of the extended second probe.

8. The method of claim 7, wherein said second probe is extended by polymerization of between 1 and 5 nucleotides.

9. The method of claim 1, wherein said second probe is corrected by cleavage of a blocking moiety present on its 3' end, and wherein said elongated second probe complex is formed by covalently ligating the 5' terminus of a third oligonucleotide probe to the 3' terminus of the corrected second probe.

10. The method of claim 1, wherein said reverse transcription comprises the use of a reverse transcriptase or a DNA polymerase.

11. The method of claim 1 wherein the length of the cDNA extension of the first probe is limited to a predetermined length by providing a combination of less than all four nucleoside triphosphate types complementary to a selected segment of target RNA.

12. The method of claim 11, wherein the length of the cDNA extension comprises a sufficient number of bases complementary to the target RNA so that said second and first probes form a stable hybridization complex under the reaction conditions.

13. The method of claim 11, wherein the length of the cDNA extension from the first probe is from about 5 to about 15 bases.

14. The method of claim 1, wherein said target RNA sequence is selected from the group consisting of genomic RNA, mRNA, tRNA, rRNA, nuclear RNA, cytoplasmic RNA, total RNA, and viral RNA and any combination thereof.

15. The method according to claim 1, wherein said amplifying step comprises at least one repeated cycle of forming both:
   (i) an elongation complex of a third oligonucleotide probe covalently ligated to the 3' terminus of said second probe and complementary to at least a portion of said first probe, with the proviso that if said second or third probe is modified, it is corrected prior to ligation of the third probe to the second probe; and
   (ii) an elongation oligonucleotide complex covalently attached to the 3' terminus of said first probe and complementary to at least a portion of said second probe.

16. The method according to claim 15, wherein said first, second and third oligonucleotide probes used in the amplifying step are identical to those used in step (e) to form the elongation probe complex.

17. The method according to claim 15, wherein said fourth oligonucleotide segment is formed by covalently ligating a fourth oligonucleotide probe to the 3' terminus of said first probe, with the proviso that said first probe is extended prior to ligation, whereby said amplification step becomes a variation of LCR.

18. The method according to claim 15, wherein said elongation oligonucleotide complex is formed solely by extension of said first probe, whereby said amplification step becomes a hybrid amplification reaction with elongation forming one elongation complex and polymerization extension forming the other elongation complex.

19. A method of amplifying a known RNA target sequence present in a biological sample, said method comprising:
   (a) treating RNA in the sample under specific hybridizing conditions with a first oligonucleotide probe which is hybridizable to a first segment of the known target RNA under said hybridizing conditions;
   (b) extending a 3' terminus of said probe by reverse transcription of the RNA target so that a cDNA segment is produced having at its 5' end said first probe and at its extended 3' end a nucleotide sequence complementary to a second segment of the target RNA, wherein the length of the cDNA extension of the first probe is limited to a predetermined length by providing a combination of less than all four nucleoside triphosphate types complementary to a selected segment of target RNA;
   (c) dissociating the extended first probe from the RNA target;
   (d) hybridizing a second oligonucleotide probe to said extended first probe, said second probe having a 3' end which, under hybridizing conditions, is hybridizable to the extended cDNA segment of the first probe but substantially not hybridizable to said first probe when the first probe is unextended;
   (e) ligating a third oligonucleotide probe, complementary to said first probe, to the 3' terminus of said second probe, with the proviso that if said second probe is extended prior to ligation, the third probe is ligated to the 3' terminus of the extended second probe, thereby to form an extended second probe complex;
   (f) ligating a fourth oligonucleotide probe, complementary to said second probe, to the 3' terminus of said first probe, with the proviso that if said first probe is extended prior to ligation, the fourth probe is ligated to the 3' terminus of the extended first probe, thereby to form an extended first probe complex; and
   (g) amplifying at least one of said extended second probe complex and said extended first probe complex by the ligase chain reaction, using the first, second, third and fourth probes as reactants, with the proviso that if said reactant probes are modified, they are corrected prior to ligation.

20. A method of forming cDNA of a predetermined length from a known RNA target sequence present in a sample, comprising the steps of:
   (a) treating RNA under specific hybridizing conditions with a first oligonucleotide probe which is hybridizable to a first segment of the target RNA under said hybridizing conditions; and
   (b) extending a 3' terminus of said probe by reverse transcription of the RNA under conditions including less than all four nucleoside triphosphate types, so that a cDNA segment of a predetermined length is produced, wherein such extension is terminated at said predetermined length when said RNA template requires a nucleoside triphosphate which is not present.

21. A method according to claim 20, further comprising dissociating the extended first cDNA probe from the RNA target and detecting said cDNA probe.

22. A method according to claim 21, further comprising amplifying said cDNA prior to said detecting step.

23. A diagnostic kit for detecting a nucleic acid target present in a biological sample, comprising in combination:
   (a) a first oligonucleotide probe which is complementary to a portion of the target;
   (b) an extending reagent for reverse transcription of an RNA target and/or extension of the first probe on a DNA target in the presence of a supply of the nucleoside triphosphates complementary to the target region 3' of the first probe, using the first probe as a primer;
   (c) a second oligonucleotide probe capable of hybridizing to said first oligonucleotide probe under hybridizing conditions substantially only when said first probe has been extended by reverse transcription;
   (d) at least one of
      (i) a third oligonucleotide probe complementary to a portion of said first probe, said probe having a 5' terminus ligatable to the 3' terminus of said second probe and complementary to a portion of said first probe, with the proviso that if said second or third probe is corrected prior to ligation, the second probe is ligatable to the third probe in their corrected form, thereby to form an elongated second probe complex; or
      (ii) a fourth oligonucleotide probe which is covalently ligatable to the 3' terminus of said first probe once it is extended, and complementary to a portion of said second probe, thereby to form an elongated first probe complex; and (e) an assembling reagent for forming the elongated second probe complex, the elongated first probe complex, or both.

24. The kit of claim 23 wherein said extending reagent comprises reverse transcriptase or DNA polymerase.

25. The kit of claim 23 wherein said assembling reagent comprises a ligase and optionally a DNA polymerase.

26. The kit of claim 23 wherein in step (d) a third oligonucleotide probe is provided.

27. The kit of claim 23 wherein in step (d) a fourth oligonucleotide probe is provided.

28. The kit of claim 26 wherein in step (d) a fourth oligonucleotide probe is also provided.

* * * * *

UNITED STATES PATENT AND TRADEMARK OFFICE
CERTIFICATE OF CORRECTION

PATENT NO. : 5,686,272
DATED : November 11, 1997
INVENTOR(S) : Marshall, et al.

It is certified that error appears in the above-identified patent and that said Letters Patent is hereby corrected as shown below:

On the title page, item [75],
In the list of Inventors please change "Racine, Wis." to --Franksville, Wis.--.

Column 39, line 38, change "oligonueleotide" to --oligonucleotide--.

Column 41, line 49, delete "specific"

Column 42, line 26, delete "specific"

Signed and Sealed this

Twenty-first Day of July, 1998

Attest:

BRUCE LEHMAN

Attesting Officer

Commissioner of Patents and Trademarks